(12) United States Patent
Manhart

(10) Patent No.: US 11,455,711 B2
(45) Date of Patent: Sep. 27, 2022

(54) PROVIDING AN OPTIMUM SUBTRACTION DATA SET

(71) Applicant: Siemens Healthcare GmbH, Erlangen (DE)

(72) Inventor: Michael Manhart, Fürth (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 0 days.

(21) Appl. No.: 17/510,935

(22) Filed: Oct. 26, 2021

(65) Prior Publication Data

US 2022/0156904 A1 May 19, 2022

(30) Foreign Application Priority Data

Nov. 13, 2020 (DE) ...................... 10 2020 214 319.8

(51) Int. Cl.
*G06T 5/50* (2006.01)
*G06T 7/11* (2017.01)
(Continued)

(52) U.S. Cl.
CPC ................ *G06T 5/50* (2013.01); *G06T 5/002* (2013.01); *G06T 7/0016* (2013.01); *G06T 7/11* (2017.01);
(Continued)

(58) Field of Classification Search
CPC ......... G06T 5/50; G06T 5/002; G06T 7/0016; G06T 7/11; G06T 7/30;
(Continued)

(56) References Cited

U.S. PATENT DOCUMENTS

| 7,386,156 B2 * | 6/2008 | Hornegger ............. A61B 6/032 |
| | | 382/130 |
| 2008/0009705 A1 * | 1/2008 | Furudate ................ A61B 5/743 |
| | | 600/410 |

(Continued)

FOREIGN PATENT DOCUMENTS

DE 102019202514 A1 8/2020

OTHER PUBLICATIONS

German Decision to Grant for German Application No. 10 2020 214 319.6 decision dated Oct. 12, 2021.

(Continued)

*Primary Examiner* — Jose L Couso
(74) *Attorney, Agent, or Firm* — Lempia Summerfield Katz LLC (57) ABSTRACT

A method for providing an optimum subtraction data set includes: receiving first image data sets acquired by a medical imaging device and which map an object under examination within a first time phase; receiving at least one second image data set acquired by the same or another medical imaging device and which maps a change in the object under examination within a second time phase; dividing the at least one second image data set into a plurality of image regions; generating subtraction image regions for the plurality of image regions; determining an image quality parameter for each subtraction image region; determining an optimum subtraction image region for each image region of the plurality of image regions of the at least one second image data set by comparing the image quality parameters; generating the optimum subtraction data set from the optimum subtraction image regions; and providing the optimum subtraction data set.

20 Claims, 5 Drawing Sheets

(51) Int. Cl.
*G06T 7/30* (2017.01)
*G06T 7/00* (2017.01)
*G06T 5/00* (2006.01)

(52) U.S. Cl.
CPC ...... *G06T 7/30* (2017.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20036* (2013.01); *G06T 2207/20224* (2013.01); *G06T 2207/30168* (2013.01)

(58) Field of Classification Search
CPC . G06T 2207/10081; G06T 2207/10088; G06T 2207/10104; G06T 2207/10116; G06T 2207/10132; G06T 2207/20036; G06T 2207/20224; G06T 2207/30168; G06T 7/0014; G06T 7/174; G06T 7/337; G06T 7/0012; G06T 2207/30101; G06T 2207/30048; G06T 2207/10121; G06T 2207/10124; G06T 2207/10128; G06T 2207/10136; G06T 2207/10072; G06T 2207/10076; G06T 2207/10084; G06T 2207/10092; G06T 2207/10096; G06T 2207/10101; G06T 2207/10108; G06T 2207/10112; G06T 2207/10056; G06T 2207/10061; G06T 2207/10064; G06T 2207/10068; G06T 2207/10016; G06T 2207/20192; G06T 2207/20228; G06T 2210/41; G06T 5/20; A61B 6/481; A61B 6/504; A61B 6/484; A61B 6/486; A61B 6/5288; A61B 6/541; A61B 6/5241; G06K 9/00496; G01R 33/5635; G16H 50/20; G16H 30/20; G16H 30/40; G16H 50/00; G16H 50/70

See application file for complete search history.

(56) References Cited

U.S. PATENT DOCUMENTS

| | | |
|---|---|---|
| 2010/0128991 A1 | 5/2010 | Weese et al. |
| 2013/0094734 A1* | 4/2013 | Rauch ............... G06T 7/38 382/130 |
| 2016/0210743 A1* | 7/2016 | Schmidt ............ A61B 5/0035 |
| 2018/0122088 A1* | 5/2018 | Ertel ................. G06T 7/0012 |
| 2018/0279983 A1 | 10/2018 | Ohishi |
| 2018/0350080 A1* | 12/2018 | Kao ................... A61B 6/481 |
| 2020/0273217 A1 | 8/2020 | Kaethner et al. |

OTHER PUBLICATIONS

Klein, Stefan, et al. "Elastix: a toolbox for intensity-based medical image registration." IEEE transactions on medical imaging 29.1 (2009): 196-205.

German Office Action for German Application No. 10 2020 214 319.6 decision dated Sep. 29, 2021.

* cited by examiner

21 - Signal to provisioning unit
24 - Signal to X-ray source
25 - Signal to display unit
26 - Signal to provisioning unit
31 - Object under examination
32 - Patient positioning device
33 - X-ray source
34 - Detector
37 - Medical x-ray device
38 - Arm
39 - Movement device
41 - Display unit
42 - Input unit
PVRS - Provisioning unit

PROVIDING AN OPTIMUM SUBTRACTION DATA SET

The present patent document claims the benefit of German Patent Application No. 10 2020 214 319.6, filed Nov. 13, 2020, which is hereby incorporated by reference in its entirety.

TECHNICAL FIELD

The disclosure relates to a method for providing an optimum subtraction data set, a medical imaging device, and a computer program product.

BACKGROUND

X-ray based imaging methods may be used to detect changes over time in an area of examination of an object under examination, for example, a human and/or animal patient. The change over time to be detected may include a spreading movement and/or flowing movement of a contrast medium, (e.g., a contrast agent flow and/or a contrast agent bolus), in a hollow organ, (e.g., a vessel section), of the object under examination.

The X-ray-based imaging methods frequently include digital subtraction angiography (DSA), wherein at least two successively acquired X-ray images which at least partially map the common area of examination are subtracted from one another. In DSA, a distinction is also frequently made between a mask phase for acquiring at least one mask image and a fill phase for acquiring at least one fill image. The mask image may map the area of examination without contrast agent. In addition, the fill image may map the area of examination while the contrast agent is present therein. DSA may produce a difference image by subtracting the mask image from the fill image. In this way, the components in the difference image that are irrelevant and/or troublesome for treatment and/or diagnostics, particularly those which are time-invariant, may be reduced and/or removed.

Movements of the object under examination, especially between the mask and fill phase, may disadvantageously cause motion artifacts in the difference image.

SUMMARY AND DESCRIPTION

The object of the present disclosure is therefore to provide improved image quality for mapping or visualizing changes in an object under examination.

The scope of the present disclosure is defined solely by the appended claims and is not affected to any degree by the statements within this summary. The present embodiments may obviate one or more of the drawbacks or limitations in the related art.

In a first aspect, the disclosure relates to a method for providing an optimum subtraction data set. In act a), first image data sets are received. The first image data sets map an object under examination within a first time phase. In addition, the first image data sets are acquired using a medical imaging device. In act b), at least one second image data set is received. The at least one second image data set maps the object under examination within a second time phase. In addition, the at least one second image data set is acquired by the same or another medical imaging device. Moreover, the at least one second image data set maps a change in the object under examination with respect to the first time phase. In act c), the at least one second image data set is divided into a plurality of image regions. Then, in act d), subtraction image regions are generated for the plurality of image regions by subtracting corresponding image regions of the first image data sets from each of the image regions of the at least one second image data set. In act e), an image quality parameter is determined for each of the subtraction image regions. Then, in act f), an optimum subtraction image region for each of the plurality of image regions of the at least one second image data set is determined by comparing the image quality parameters. In act g), the optimum subtraction data set is generated from the optimum subtraction image regions. The optimum subtraction data set is then provided in act h).

The receiving of the first image data sets and/or the at least one second image data set may include detecting and/or reading a computer-readable data memory and/or receiving from a data storage unit, for example, a database. The first image data sets may also be provided by a provisioning unit of the medical imaging device. In addition, the at least one second image data set may be provided by a provisioning unit of the same and/or another medical imaging device.

The object under examination may be a human and/or animal patient. The object under examination may also have an area of examination. In particular, the area of examination may include a spatial section, in particular a volume, of the object under examination, containing a hollow organ. The hollow organ may include a lung and/or a vessel section, (e.g., an artery and/or vein), and/or a heart.

The first image data sets may advantageously include a two-dimensional (2D) and/or three-dimensional (3D) mapping or visualization of the object under examination, in particular of the area of examination. In addition, the first image data sets may map the object under examination in a time-resolved manner. In particular, the first image data sets may map the object under examination at different points in time in each case. The first image data sets may also be reconstructed from a plurality of first individual images, in particular a plurality of first projection images, each including a mapping or visualization of at least one section of the object under examination. In addition, the first image data sets may include metadata, wherein the metadata may include information about an acquisition parameter and/or operating parameter of the medical imaging device.

The first image data sets may advantageously map the object under examination within a first time phase, in particular a mask phase. For this purpose, the first image data sets may advantageously be acquired within a predefined first time period.

The at least one second image data set may advantageously include a two-dimensional (2D) and/or three-dimensional (3D) mapping or visualization of the object under examination, in particular of the area of examination. In addition, the at least one second image data set may map the object under examination in a time-resolved manner. The at least one second image data set may also be reconstructed from a plurality of second individual images, in particular a plurality of second projection images, each including a mapping or visualization of at least one section of the object under examination. In addition, the at least one second image data set may include metadata, wherein the metadata may include information about an acquisition parameter and/or operating parameter of the medical imaging device.

The at least one second image data set may advantageously map the object under examination within a second time phase, in particular a fill phase. For this purpose, the at least one second image data set may advantageously be acquired within a predefined second time period. Advantageously, the second time phase may be downstream of the first time phase.

In addition, the at least one second image data set may map a change in the object under examination compared to the first time phase. The change in the object under examination may be a contrast agent, in particular a contrast agent flow, and/or a medical object, in particular a diagnostic and/or surgical instrument disposed at least partially in the object under examination during the second time phase. In particular, the change in the object under examination may include a change over time and/or a spatial change.

The first image data sets and/or the at least one second image data set may advantageously each have a plurality of image points, in particular pixels and/or voxels. If the first image data sets and/or the at least one second image data set are time-resolved, the image points may also each have a time intensity curve.

In act c), the at least one second image data set may advantageously be divided into a plurality of, in particular spatial, image regions. Advantageously, the image regions may at least partially adjoin each other, in particular without overlapping, and/or at least partially overlap. An image region (also termed a patch) may have at least one image point, in particular a plurality of image points, of the at least one second image data set. The division of the at least one second image data set into the plurality of image regions may advantageously be performed uniformly and/or non-uniformly in respect of a spatial extent of the image regions. For example, the at least one second image data set may be divided into the plurality of image regions in a grid-like manner. The image regions may each have the same number of image points of the at least one second image data set.

In act d), subtraction image regions may advantageously be generated for the plurality of image regions by subtracting in particular spatially corresponding image regions of the first image data sets from each of the image regions of the at least one second image data set. Advantageously, for each of the image regions of the at least one second image data set, there may be a spatially corresponding image region in each of the first image data sets. Act d) may include identifying the image regions of the first image data sets corresponding to the image regions of the at least one second image data set.

Provided that the first image data sets and the at least one second image data set are acquired by the same medical imaging device, the first and second image data sets may each be registered, in particular inherently, with respect to a common coordinate system. Alternatively, or additionally, act d) may include registration, in particular a motion correction, of the first image data sets and/or the at least one second image data set. The corresponding image regions of the first image data sets may each have at least one image point, (e.g., a plurality of image points), of the respective first image data set, in particular similarly to the image regions of the at least one second image data set. In addition, the image regions of the first image data sets which correspond to the image regions of the at least one second image data set may be identified on the basis of the spatial disposition of the respective image points, in particular in the common coordinate system. Alternatively, or additionally, the corresponding image regions may be identified on the basis of geometric and/or anatomical features mapped in the first image data sets and the at least one second image data set.

To generate the subtraction image regions, the corresponding image regions of, in particular, all the first image data sets may advantageously be subtracted from, in particular, all the image regions of the at least one second image data set. Thus, a plurality of subtraction image regions may be generated for, in particular, all the image regions of the at least one second image data set in each case. Advantageously, the subtraction image regions may each map the differences, in particular the change, in the object under examination between the first and the second time phase. In addition, the subtraction image regions may have image artifacts that may be caused by motion of the object under examination between the acquisition of the first image data sets and/or of the at least one second image data set.

In act e), an image quality parameter may be determined for the subtraction image regions, in particular for each of the subtraction image regions. Advantageously, the image quality parameters may evaluate an artifact level, in particular a severity of image artifacts, and/or a signal-to-noise ratio (SNR) in the respective subtraction image region. The image quality parameter may therefore have a value, in particular a normalized value, which evaluates the image quality of the respective subtraction image region.

Accordingly, in act f), the image quality parameters of the subtraction image regions, each corresponding to a common image region of the at least one second image data set, may be compared. Advantageously, by comparing the image quality parameters, the subtraction image region having an optimum image quality parameter in respect of image quality may be selected from the plurality of subtraction image regions for each of the image regions of the at least one second image data set. This subtraction image region may subsequently be provided as the optimum subtraction image region for the respective image region of the at least one second image data set.

By comparing the image quality parameters for selecting the respective optimum subtraction image region for in particular all the image regions of the at least one second image data set from the respective plurality of subtraction image regions, the subtraction image regions which exhibit image artifacts, in particular motion artifacts and/or metal artifacts, and/or noise may advantageously be eliminated.

Consequently, in act d) the optimum subtraction image regions may have been generated in each case by subtracting the in particular spatially corresponding image region of the first image data set from the respective image region of the at least one second image data set, the corresponding image region having the greatest possible correspondence with the image region of the at least one second image data set with respect to positioning of the object under examination and/or minimal noise and/or minimal image artifacts.

The generation of the optimum subtraction data set in act g) may include joining and/or assembling the optimum subtraction image regions to form the optimum subtraction data set. The joining and/or assembling of the optimum subtraction image regions to form the optimum subtraction data set may be performed in accordance with a spatial positioning of the section of the area of examination mapped in each of the optimum subtraction image regions. Advantageously, the optimum subtraction data set may map the differences, in particular the change, in the object under examination between the first and the second time phase.

In addition, providing the optimum subtraction data set in act h) may include storing the optimum subtraction data set on a computer-readable storage medium and/or displaying the optimum subtraction data set on a display unit and/or transmitting the optimum subtraction data set to a provisioning unit. In particular, a graphical representation of the optimum subtraction data set may be displayed on the display unit.

The proposed embodiment enables the image quality of subtraction data sets to be improved. If the examination object moves during and/or between acquisition of the first image data sets and/or the at least one second image data set, motion artifacts in the optimum subtraction data set may be advantageously minimized by the proposed method. In particular, improved perfusion imaging may be achieved by the proposed method in that perfusion maps may be calculated from the optimum subtraction data set.

In a further advantageous embodiment of the proposed method, act f) may include act f.2) in which it may be checked whether the number of first image data sets which were used for generating the optimum subtraction image regions exceeds a predetermined threshold value. If so, the first image data set that was used least frequently to generate the optimum subtraction image regions may be identified. In addition, the at least one optimum subtraction image region which was generated by the identified first image data set may be replaced by the subtraction image region which has a next best image quality parameter. Act f.2) may be executed repeatedly until the predetermined threshold value is reached or undershot.

The optimum subtraction image regions may have been generated in act d) in each case by subtracting the respective, in particular spatially corresponding image region of the first image data set from the image regions of the at least one second image data set, the corresponding image region having the greatest possible correspondence with the image region of the at least one second image data set and/or minimal noise and/or minimal image artifacts with regard to positioning of the object under examination. This may be provided by comparing the image quality parameters for determining the optimum subtraction image regions in act f). The optimum subtraction regions in act d) may have been generated from corresponding image regions of one or more of the first image data sets.

Advantageously, the subtraction image regions may be assigned to each of the image regions of the at least one second image data set according to their image quality parameters, for example, by arranging them in a corresponding data structure and/or by assignment of an ordinal number.

Act f.2) may advantageously include comparing the number of first image data sets whose corresponding image regions were used to generate the optimum subtraction image regions, in particular also to generate the optimum subtraction data set, with the predetermined threshold value. For example, the threshold value may be predetermined and/or adjusted by a user input to an input unit. The threshold value may also be predetermined as a function of the number of image regions. Alternatively, or in addition, the predetermined threshold value may be predetermined as a function of a number and/or image property, for example a spatial resolution, of the first image data sets received in act a) and/or of the at least one second image data set.

If the check in act f.2) shows that the threshold value is exceeded, the first image data set whose corresponding image regions were used least frequently to generate the subtraction image regions determined as optimum in act f) may advantageously be identified. If a plurality of first image data sets are identified in act f.2), which in particular were used equally frequently to generate the subtraction image regions determined as optimum in act f), the first image data set to be replaced may be identified by comparing the image quality parameters of the optimum subtraction areas generated from the identified first image data sets in each case.

Advantageously, the at least one optimum subtraction image region, which was generated by the identified first image data set, may be replaced by the in particular spatially corresponding subtraction image region having the next best image quality parameter. This may advantageously reduce the number of first image data sets used to generate the optimum subtraction image regions.

Advantageously, act f.2) may be executed repeatedly until the predetermined threshold value is reached or undershot. This may advantageously provide that the number of first image data sets used to generate the optimum subtraction image regions does not exceed the predetermined threshold value. In addition, it may advantageously reduce any variance between the optimum subtraction image regions in the optimum subtraction data set.

In another advantageous embodiment of the proposed method, act f) may additionally include acts f.3) and f.4). In act f.3), the optimum subtraction image regions may be classified into spatially coherent and spatially isolated optimum subtraction image regions. Spatially adjacent optimum subtraction image regions which were generated using the same first image data set may be classified as spatially coherent. In addition, optimum subtraction image regions without a spatially adjacent optimum subtraction image region generated using the same first image data set may be classified as spatially isolated. In addition, in act f.4), the spatial component of the classified optimum subtraction image regions may be compared with a comparison component. If the comparison component is undershot, the at least one optimum subtraction image region may advantageously be replaced by the subtraction image region, in particular the spatially corresponding subtraction image region, which has the next best image quality parameter. Acts f.3) and f.4) may also be repeated until the spatial components of the classified optimum subtraction image regions reach or exceed the comparison component.

The classification of the optimum subtraction image regions into spatially coherent and spatially isolated optimum subtraction image regions may include binary identification and/or masking of the optimum subtraction image regions according to their respective spatial arrangement. Advantageously, optimum subtraction image regions which have directly adjacent image points may be considered as spatially adjacent optimum subtraction image regions. Similarly, optimum subtraction image regions that do not have adjacent image points may be considered as spatially non-adjacent optimum subtraction image regions.

The optimum subtraction image regions may have been generated in each case in act d) by subtracting the in particular spatially corresponding image region of the first image data set from the image regions of the at least one second image data set in each case, the corresponding image region having the greatest possible correspondence with the image region of the at least one second image data set in respect of positioning of the object under examination and/or minimal noise and/or minimal image artifacts. This may be provided by comparing the image quality parameters for determining the optimum subtraction image regions in act f). The optimum subtraction regions in act d) may have been generated from corresponding image regions of one or more of the first image data sets. If an optimum subtraction region is spatially adjacent to another optimum subtraction region, the further optimum subtraction region having been generated by the same first image data set in act d), the optimum subtraction region and the other optimum subtraction region may be classified as spatially coherent. If one of the optimum subtraction regions does not have a spatially adjacent other optimum subtraction region which has been generated by the same first image data set in act d), this optimum subtraction region may be classified as spatially isolated.

Advantageously, a spatial component of the classified optimum subtraction image regions may be determined in each case in act f.4). In particular, the spatial component may be determined as the area and/or volume of the respective optimum subtraction image regions classified as spatially coherent or spatially isolated with respect to a total area and/or a total volume of all the optimum subtraction image regions. Alternatively, or in addition, the respective spatial component of the classified optimum subtraction image regions may be determined with respect to an area and/or a volume of the first image data sets and/or of the at least one second image data set.

Act f.4) may also include a comparison between the respective spatial components of the classified optimum subtraction image regions with the comparison component. The comparison component may be predetermined and/or adjusted by a user by another user input to an input unit. The comparison component may also be predetermined as a function of the number of image regions. Alternatively, or additionally, the comparison component may be predetermined as a function of a number and/or image property, for example a spatial resolution, of the first image data sets received in act a) and/or of the at least one second image data set.

If the comparison shows that the spatial component of at least one of the classified optimum subtraction image regions is below the comparison component, the at least one optimum subtraction image region may be replaced by the in particular spatially corresponding subtraction image region which has the next best image quality parameter.

In particular, in act f.4), the spatial component of optimum subtraction image regions classified as spatially isolated may be compared with the comparison component. If the comparison component is undershot, the respective optimum subtraction image region classified as spatially isolated may advantageously be replaced by the in particular spatially corresponding subtraction image region which has the next best image quality parameter.

Acts f.3) and f.4) may be advantageously repeated until the spatial components of the classified optimum subtraction image regions reach or exceed the comparison component. Advantageously, parcellation of in particular spatially isolated optimum subtraction image regions may be reduced in the optimum subtraction data set.

In another advantageous embodiment of the proposed method, optimum subtraction image regions classified as spatially isolated may be integrated into an optimum subtraction image region classified as spatially coherent by applying a morphological operation.

The morphological operation may include dilating one of the optimum subtraction image regions classified as spatially coherent that is adjacent to an optimum subtraction image region classified as spatially isolated. Alternatively, or additionally, the morphological operation may include eroding an optimum subtraction image region classified as spatially isolated. The morphological operation may relate to image values of image points of an optimum subtraction image region classified as spatially isolated. The morphological operation may relate to replacing, in particular pixel by pixel, an optimum subtraction image region classified as spatially isolated by an adjacent optimum subtraction image region classified as spatially coherent.

This may advantageously reduce the number of optimum subtraction image regions classified as spatially isolated. It may improve the image quality of the optimum subtraction data set still further.

In another advantageous embodiment of the proposed method, in act f), the optimum subtraction image regions may also be classified into spatially coherent and spatially isolated optimum subtraction image regions. The spatially adjacent optimum subtraction image regions, which were generated by the same first image data set, may be classified as spatially coherent. In addition, optimum subtraction image regions without a spatially adjacent optimum subtraction image region generated using the same first image data set may be classified as spatially isolated. The optimum subtraction image regions classified as spatially isolated may be integrated into an optimum subtraction image region classified as spatially coherent by applying a morphological operation.

The morphological operation may have all the features and properties described in respect of the previously described advantageous embodiment of the proposed method. In addition, the classification of the optimum subtraction image regions into spatially coherent and spatially isolated optimum subtraction image regions may be performed in a similar manner to act f.3) of another advantageous embodiment of the proposed method described above.

This may advantageously reduce the number of optimum subtraction image regions classified as spatially isolated. Moreover, the image quality of the optimum subtraction data set may be improved still further.

In another advantageous embodiment of the proposed method, act d) may include d.2) in which the image regions of the at least one second image data set may be registered to align with the corresponding image regions of the first image data sets.

Registration of the image regions of the at least one second image data set to align with the respective corresponding image regions of the first image data sets may advantageously include a rigid and/or non-rigid spatial transformation of the image regions and/or the corresponding image regions, for example, translation and/or rotation and/or deformation and/or scaling. In particular, registering the image regions of the at least one second image data set with the respective corresponding image regions of the first image data sets may include motion correction. In particular, the registration may be based on anatomical and/or geometric features and/or a marker object which may be mapped in the first image data sets and/or the at least one second image data set, and/or metadata.

Advantageously, by registering the image regions of the at least one second image data set to align with the corresponding image regions of the first image data sets, the image quality of the in particular optimum subtraction image regions generated therefrom may be improved. In addition, this may also improve the image quality of the optimum subtraction data set. In particular, image artifacts in the optimum subtraction data set that may be caused, for example, by misalignment between the mapping or visualization of the object under examination in the first image data sets and the at least one second image data set may be reduced.

In another advantageous embodiment of the proposed method, act g) may include combining spatially adjacent optimum subtraction image regions in at least one common edge region.

The optimum subtraction image regions, which are spatially adjacent to each other, may advantageously have at least one image point in each case, the image points being in particular directly spatially adjacent to one another. This at least one image point may advantageously be disposed on a boundary line and/or boundary area between the spatially adjacent optimum subtraction image regions. In particular, the at least one common edge region may contain the image points of the respective adjacent optimum subtraction image regions, the image points being disposed on the common boundary line and/or boundary area. The common edge region may also include further image points of the respective spatially adjacent optimum subtraction image regions which are disposed within a predefined spatial distance, in particular in a strip-shaped manner, around the common boundary line and/or boundary area.

Advantageously, act g) may include a combination, for example, of weighted averaging and/or interpolation of the respective spatially adjacent optimum subtraction image regions, in particular of the image points which are disposed within the common boundary area. Edges and/or gradations in the optimum subtraction data set which may result from assembling and/or joining the optimum subtraction image regions at the boundary lines and/or boundary areas may advantageously be reduced, in particular smoothed, by this method.

In another advantageous embodiment of the proposed method, the dividing of the at least one second image data set into the plurality of image regions in act c) may be performed on the basis of anatomical and/or geometric features mapped in the at least one second image data set.

The anatomical and/or geometric features may include a mapping or visualization of an organ, (e.g., a hollow organ), and/or a tissue of the object under examination and/or a marker structure outline. In particular, act c) may include identifying, (e.g., segmenting), the anatomical and/or geometric features in the at least one second image data set. The subdividing may include comparing image values of the image points of the at least one second image data set with at least one predetermined threshold value. Alternatively, or additionally, the segmenting may be performed using an anatomy atlas. The segmenting of the at least one second image data set into the plurality of image regions may advantageously be performed on the basis of the identified anatomical and/or geometric features.

This advantageously enables the image regions to include as completely as possible an anatomical and/or geometric feature that is mapped in the at least one second image data set. In particular, the image regions may each be regarded as a region of interest (ROI).

This may advantageously avoid subdividing anatomical structures and/or geometric features, (e.g., an outline), which may be mapped in the at least one second image data set, into different image regions.

In another advantageous embodiment of the proposed method, the at least one second image data set may map a contrast agent disposed in the object under examination in the second time phase as the change.

The contrast agent may be an X-ray contrast agent, (e.g., a radiopaque contrast agent), and/or an ultrasound contrast agent and/or a magnetic resonance contrast agent. Advantageously, the contrast agent may have been applied to the object under examination before the start of the proposed method. Advantageously, the contrast agent disposed at least partially in the region under examination, in particular a spreading of the contrast agent and/or a contrast agent bolus, may be mapped in the at least one second image data set.

The contrast agent may advantageously be disposed, in particular selectively, during the second time phase in the hollow organ to be mapped in the object under examination. This advantageously enables a contrasted image of the hollow organ to be obtained in the at least one second image data set and consequently in the subtraction image regions.

In another advantageous embodiment of the proposed method, the image quality parameters in act e) may be determined by applying an image quality metric to each of the subtraction image regions. The image quality metric may also evaluate the artifact level and/or signal-to-noise ratio in the respective subtraction image region.

The image quality metric may advantageously be configured to evaluate an occurrence and/or severity of image artifacts, for example, motion artifacts and/or metal artifacts and/or reconstruction artifacts, in the subtraction image regions. For each of the subtraction image regions, the image quality metric may advantageously provide an in particular normalized image quality parameter which evaluates the artifact level and/or signal-to-noise ratio in the respective subtraction image region. In addition, the image quality metric may be based on entropy and/or total variation in the subtraction image regions. The image quality metric may also include a consistency condition in respect of the image features that may be contained in the first image data sets and/or the at least one second image data set and/or the respective subtraction image region.

This may advantageously provide a uniform and/or standardized evaluation of the image quality of the subtraction image regions. Moreover, it enables the determining, in particular the selection, of the respective optimum subtraction image region for the plurality of image regions of the at least one second image data set to be made possible by comparing the image quality parameters.

In another advantageous embodiment of the proposed method, the image quality metric may be based on artificial intelligence.

Advantageously, the image quality metric may be trained by a machine learning method. In particular, the image quality metric may include a trained function which has been trained by a machine learning method. The image quality metric, in particular the trained function, may be a neural network, in particular a convolutional neural network (CNN) or a network including a convolutional layer.

The trained function maps input data to output data. In particular, the output data may further depend on one or more parameters of the trained function. The one or more parameters of the trained function may be determined and/or adjusted by training. In particular, determining and/or adjusting the one or more parameters of the trained function may be based on a pairing of training input data and associated comparison output data, wherein the trained function is applied to the training input data to generate training mapping data. In particular, the determining and/or adjusting may be based on a comparison of the training mapping data and the comparison output data. A trainable function, (e.g., a function having one or more parameters that have not yet been adjusted), may also referred to as a trained function.

Other terms for trained function are trained mapping rule, mapping rule with trained parameters, function with trained parameters, artificial intelligence based algorithm, machine learning algorithm. An example of a trained function is an artificial neural network, wherein the edge weights of the artificial neural network correspond to the parameters of the trained function. Instead of the term "neural network," the term "artificial neural network" may also be used. In particular, a trained function may also be a deep artificial neural network. Another example of a trained function is a "support vector machine," and also other machine learning algorithms in particular may be used as trained functions.

In particular, the trained function may be trained using back propagation. First, training mapping data may be determined by applying the trained function to training input data. Any deviation between the training mapping data and the comparison output data may then be determined by applying an error function to the training mapping data and the comparison output data. In addition, at least one parameter, (e.g., a weighting), of the trained function, (e.g., the neural network), may be iteratively adjusted based on a gradient of the error function with respect to the at least one parameter of the trained function. This may advantageously minimize the deviation between the training mapping data and the comparison output data during the training of the trained function.

Advantageously, the trained function, in particular the neural network, has an input layer and an output layer. The input layer may be configured to receive input data. In addition, the output layer may be configured to provide mapping data. The input layer and/or the output layer may each include a plurality of channels, in particular neurons.

The image quality metric, in particular the trained function, may be configured to process a subtraction image range as input data and provide the image quality parameter as output data.

For training the image quality metric, in particular the trained function, training input data having training subtraction image regions may be determined by applying acts a) to d) to first and second training image data sets. In particular, the first and second training image data sets may have all the features and characteristics of the first image data sets and the at least one second image data set. In particular, the first and/or second training image data sets may be simulated. In addition, simulating at least one part of the first and/or second image data sets may include applying an in particular rigid and/or non-rigid transformation to one of the first and/or second image data sets. This means that, for example, motion artifacts that may be caused by movement of the object under examination may be advantageously simulated for the training of the trained function.

In addition, the comparison output data may be determined by applying at least one other image quality metric to the training input data. For example, the at least one other image quality metric may be based on entropy and/or total variation of the training input data. Alternatively, or in addition, the comparison output data may be determined by annotation of the training input data, for example, by a user input which evaluates the image quality of the training input data. In addition, the training may be performed in particular by supervised training.

This provides a particularly robust and precise determination of the image quality parameters in act e).

In another advantageous embodiment of the proposed method, the medical imaging device and/or the additional medical imaging device may be a medical X-ray device and/or a computed tomography (CT) device and/or a magnetic resonance imaging (MRI) device and/or a positron emission tomography (PET) device and/or an ultrasound device.

This means that an imaging modality tailored in particular to the change to be mapped in the object under examination may be used for acquiring and/or providing the first image data sets and/or the at least one second image data set.

In a second aspect, the disclosure relates to a medical imaging device configured to carry out a proposed method for providing an optimum subtraction data set.

The medical imaging device may be configured as a medical X-ray device, (e.g., a medical C-arm X-ray device), and/or a computed tomography (CT) device and/or a magnetic resonance imaging (MRI) device and/or a positron emission tomography (PET) device and/or an ultrasound device. The medical imaging device may advantageously have a provisioning unit configured to execute the acts of the proposed method.

The advantages of the proposed medical imaging device correspond to the advantages of the proposed method for providing an optimum subtraction data set. Features, advantages, or alternative embodiments mentioned herein may equally be applied to the other claimed subject matters and vice versa.

In a third aspect, the disclosure relates to a computer program product including a computer program directly loadable into a memory of a provisioning unit and including program sections for executing all the acts of the proposed method for providing an optimum subtraction data set when the program sections are executed by the provisioning unit. The computer program product may include software having source code that still needs to be compiled and bound or that only needs to be interpreted, or executable software code that only needs to be loaded into the provisioning unit for execution. The computer program product enables the method of providing an optimum subtraction data set using a provisioning unit to be executed in a fast, identically repeatable, and robust manner. The computer program product is configured to carry out the method acts by the provisioning unit.

The computer program product is stored, for example, on a computer-readable storage medium or installed on a network or server, from where the computer program product may be loaded into the provisioning unit's processor which may be directly connected to the provisioning unit or implemented as part of the provisioning unit. In addition, control information of the computer program product may be stored on an electronically readable data carrier. The control information of the electronically readable data carrier may be configured to carry out a method when the data carrier is used in a provisioning unit. Examples of electronically readable data carriers are a DVD, a magnetic tape, or a USB stick on which electronically readable control information, in particular software, is stored. If this control information is read from the data carrier and stored in a provisioning unit, all the embodiments of the above described methods may be carried out.

The disclosure may also proceed from a computer-readable storage medium and/or electronically-readable data carrier having stored thereon program sections that may be read and executed by a provisioning unit in order to execute all the acts of the method for providing an optimum subtraction data set when the program sections are executed by the provisioning unit.

The advantage of a largely software-based implementation is that provisioning units already in use may also be upgraded in a simple manner by a software update in order to operate in the manner according to the disclosure. In addition to the computer program, such a computer program product may if necessary include additional elements, such as documentation and/or additional components, as well as hardware components, such as hardware keys (dongles, etc.) for using the software.

BRIEF DESCRIPTION OF THE DRAWINGS

Exemplary embodiments of the disclosure are illustrated in the accompanying drawings and will be described in more detail below. The same reference characters are used for identical features in the different figures.

DETAILED DESCRIPTION

Figure 1:
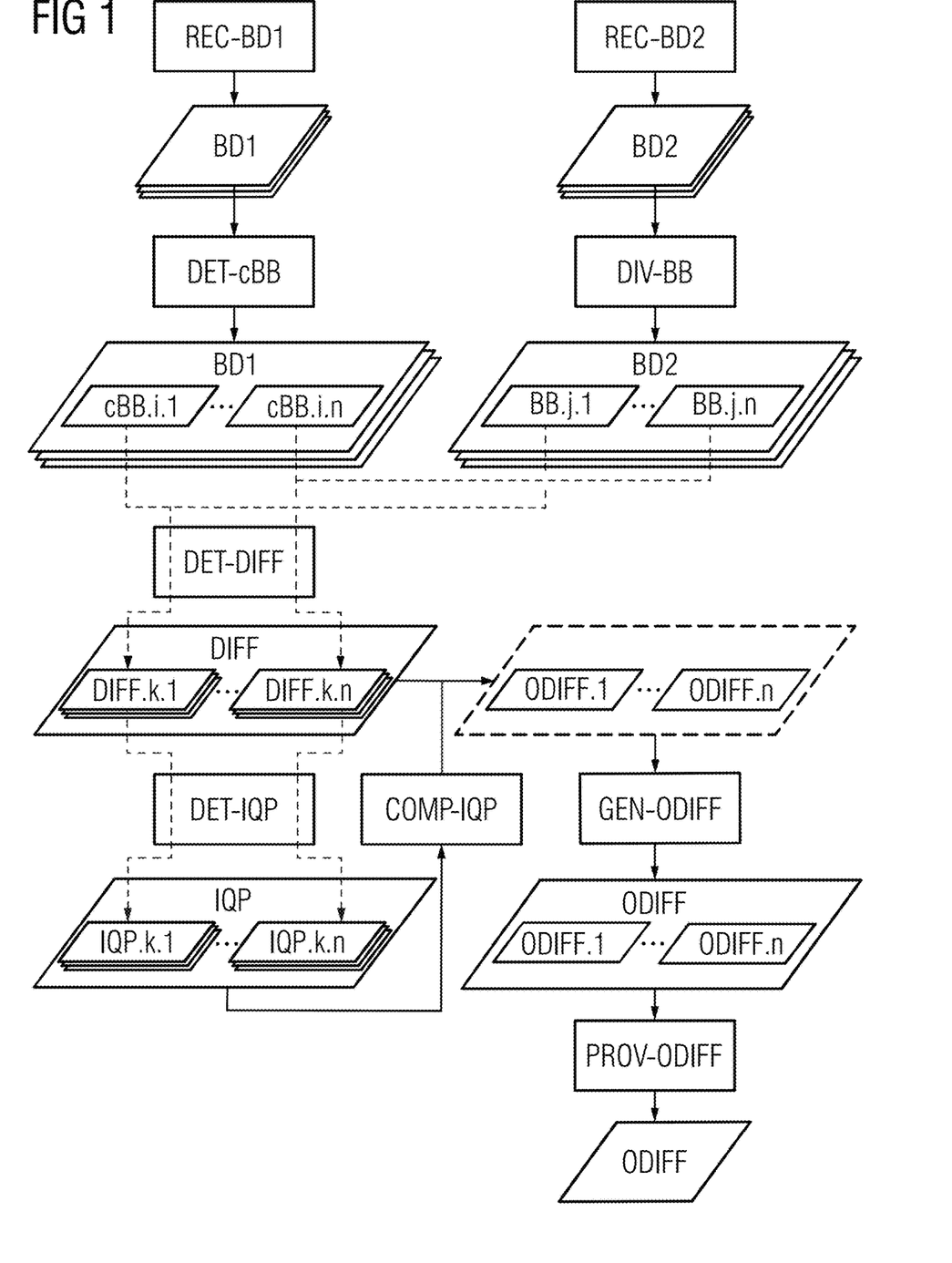
FIGS. 1 to 4 schematically illustrate various embodiments of a method for providing an optimum subtraction data set.

FIG. 1 shows a schematic representation of an advantageous embodiment of a proposed method for providing an optimum subtraction data set. In act a), first image data sets BD1 may be received REC-BD1. The first image data sets BD1 may map an object under examination within a first time phase. The first image data sets BD1 may also have been acquired by a medical imaging device. In act b), at least one second image data set BD2 may be received REC-BD2. The at least one second image data set BD2 may map the object under examination within a second time phase. In addition, the at least one second image data set BD2 may be acquired by the same or another medical imaging device.

The medical imaging device and/or the other medical imaging device may be configured as a medical X-ray device, (e.g., a medical C-arm X-ray device), and/or a computed tomography system and/or a magnetic resonance system and/or a positron emission tomography system and/or an ultrasound device.

In addition, the at least one second image data set BD2 may map a change in the object under examination relative to the first time phase. In particular, the at least one second image data set BD2 may map a contrast agent disposed in the object under examination in the second time phase as the change. In act c), the at least one second image data set BD2 may be divided into a plurality of image regions BB.j.1 to BB.j.n DIV-BB. In act d), subtraction image regions DIFF.k.1 to DIFF.k.n may be generated DET-DIFF for the plurality of image regions BB.j.1 to BB.j.n by subtracting corresponding image regions cBB.i.1 to cBB.i.n of the first image data sets BD1 from respective image regions BB.j.1 to BB.j.n of the at least one second image data set BD2. For this purpose, the corresponding image regions cBB.i.1 to cBB.i.n of the first image data sets BD1 may first be determined DET.cBB. The corresponding image regions cBB.i.1 to cBB.i.n of the first image data sets BD1 may be identified, for example, on the basis of the spatial disposition of the respective image points, in particular in a common coordinate system. Alternatively, or additionally, the corresponding image regions cBB.i.1 to cBB.i.n may be identified on the basis of geometric and/or anatomical features mapped in the first image data sets BD1 and the at least one second image data set BD2.

In act e), an image quality parameter IQP.k.1 to IQP.k.n may be determined for the subtraction image regions DIFF.k.1 to DIFF.k.n respectively. Then, in act f), an optimum subtraction image region ODIFF.1 to ODIFF.n may be determined for the plurality of image regions BB.j.1 to BB.j.n respectively of the at least one second image data set BD2 by comparing COMP-IQP the image quality parameters IQP.k.1 to IQP.k.n.

In act g), the optimum subtraction data set ODIFF may be generated GEN-ODIFF from the optimum subtraction image regions ODIFF.1 to ODIFF.n. The optimum subtraction data set ODIFF may then be provided PROV-ODIFF in act h).

Advantageously, act d) may include act d.2), wherein the image regions BB.j.1 to BB.j.n of the at least one second image data set BD2 may be registered with the corresponding image regions cBB.i.1 to cBB.i.n of the first image data sets.

In addition, act g) may include combining spatially adjacent optimum subtraction image regions ODIFF.1 to ODIFF.m in at least one common edge region.

Advantageously, the division DIV-BB of the at least one second image data set BD2 into the plurality of image regions BB.j.1 to BB.j.n may take place in act c) based on anatomical and/or geometric features mapped in the at least one second image data set BD2.

The at least one second image data set BD2 may also map a contrast agent disposed in the object under examination in the second time phase as the change.

In addition, the image quality parameters IQP may be determined in act e) by applying an image quality metric to each of the subtraction image regions DIFF.k.1 to DIFF.k.n. The image quality metric may evaluate an artifact level and/or signal-to-noise ratio in the respective subtraction image region DIFF.k.1 to DIFF.k.n. The image quality metric may also be based on artificial intelligence.

In FIGS. 1 to 4, the corresponding image regions cBB.i.1 to cBB.i.n of one, in particular the i-th, of the plurality of first image data sets BD1 are shown as representative of the corresponding image regions of the plurality of first image data sets BD1. For example, the first image data sets BD1 may each have a number n of corresponding image regions. If a plurality of second image data sets are received in act b), the image regions BB.j.1 to BB.j.n of one, in particular the j-th, of the plurality of second image data sets BD2, are shown as representative of the image regions of the plurality of second image data sets BD2. The second image data sets BD2 may each have a number n of image regions, in particular similarly to the first image data sets. In addition, the image quality parameters IQP.k.1 to IQP.k.n and the subtraction image regions DIFF.k.1 to DIFF.k.n for an, in particular, k-th subtraction of corresponding image regions cBB.i.1 to cBB.i.n of an, in particular, i-th first image data set BD1 from each of the image regions BB.j.1 to BB.j.n of an, in particular, j-th second image data set BD2 are schematically illustrated.

Figure 2:
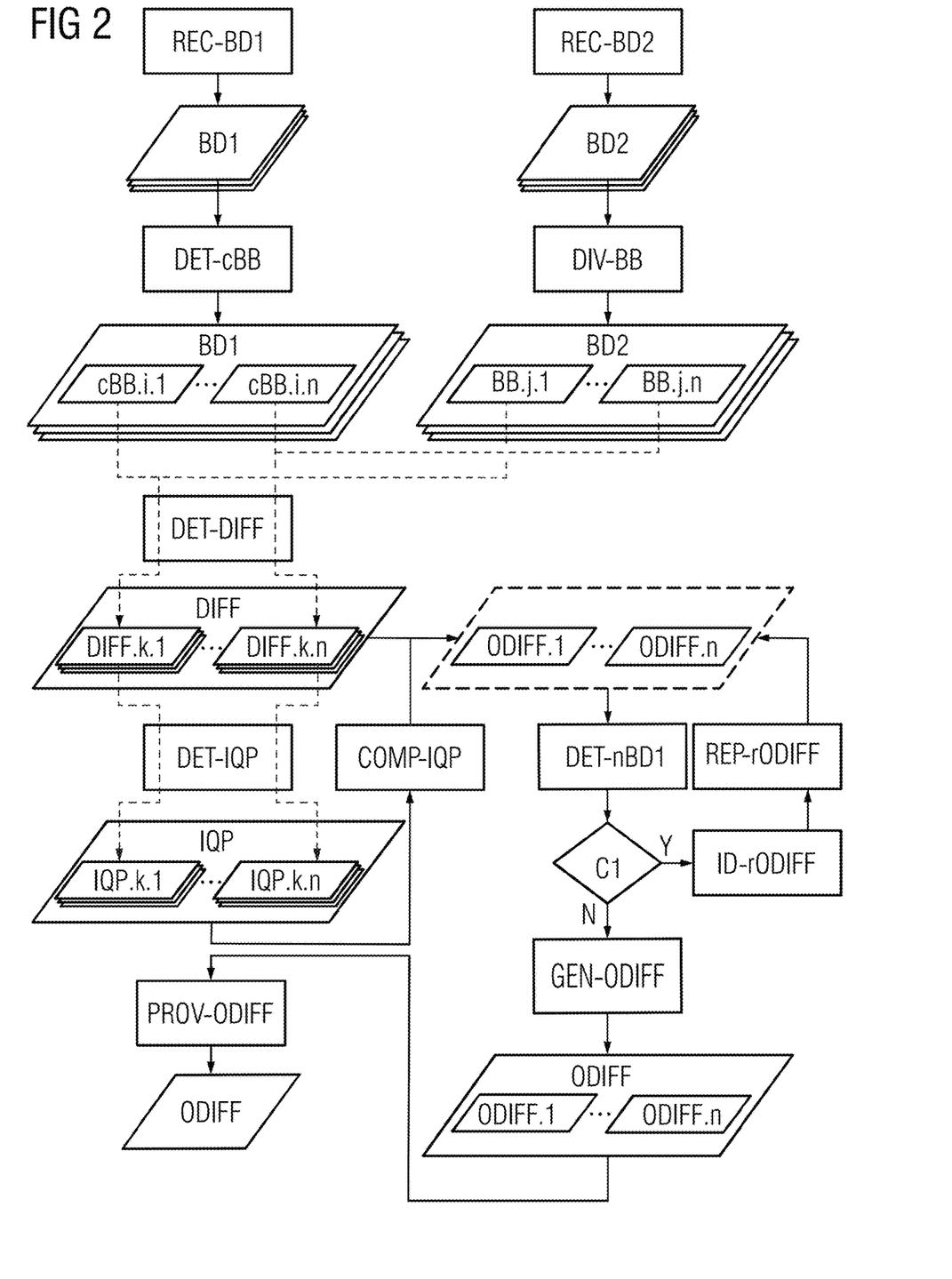

Another advantageous embodiment of the proposed method for the provision PROV-ODIFF of an optimum subtraction data set ODIFF is represented schematically in FIG. 2. Here a number of first image data sets BD1 may be determined DET-nBD1 which were used to generate the optimum subtraction image regions ODIFF.1 to ODIFF.n. Then, in act f.2), it may be checked whether the number of first image data sets, the first image data sets BD1 having been used to generate the optimum subtraction image regions ODIFF.1 to ODIFF.n, exceeds a predetermined threshold value. In particular, the checking may involve a comparison C1 of the number with the predetermined threshold value. If this is the case Y, the first image data set BD1 that was used least frequently to generate the optimum subtraction image regions ODIFF.1 to ODIFF.n may be identified ID-rODIFF. In addition, the at least one optimum subtraction image region ODIFF.1 to ODIFF.n which was generated using the identified first image data set BD1 may be replaced REP-rODIFF by the subtraction image region DIFF.1 to DIFF.n which has a next best image quality parameter IQP.1 to IQP.n. Act f.2) may then be repeated until the threshold value is reached or undershot N.

Figure 3:
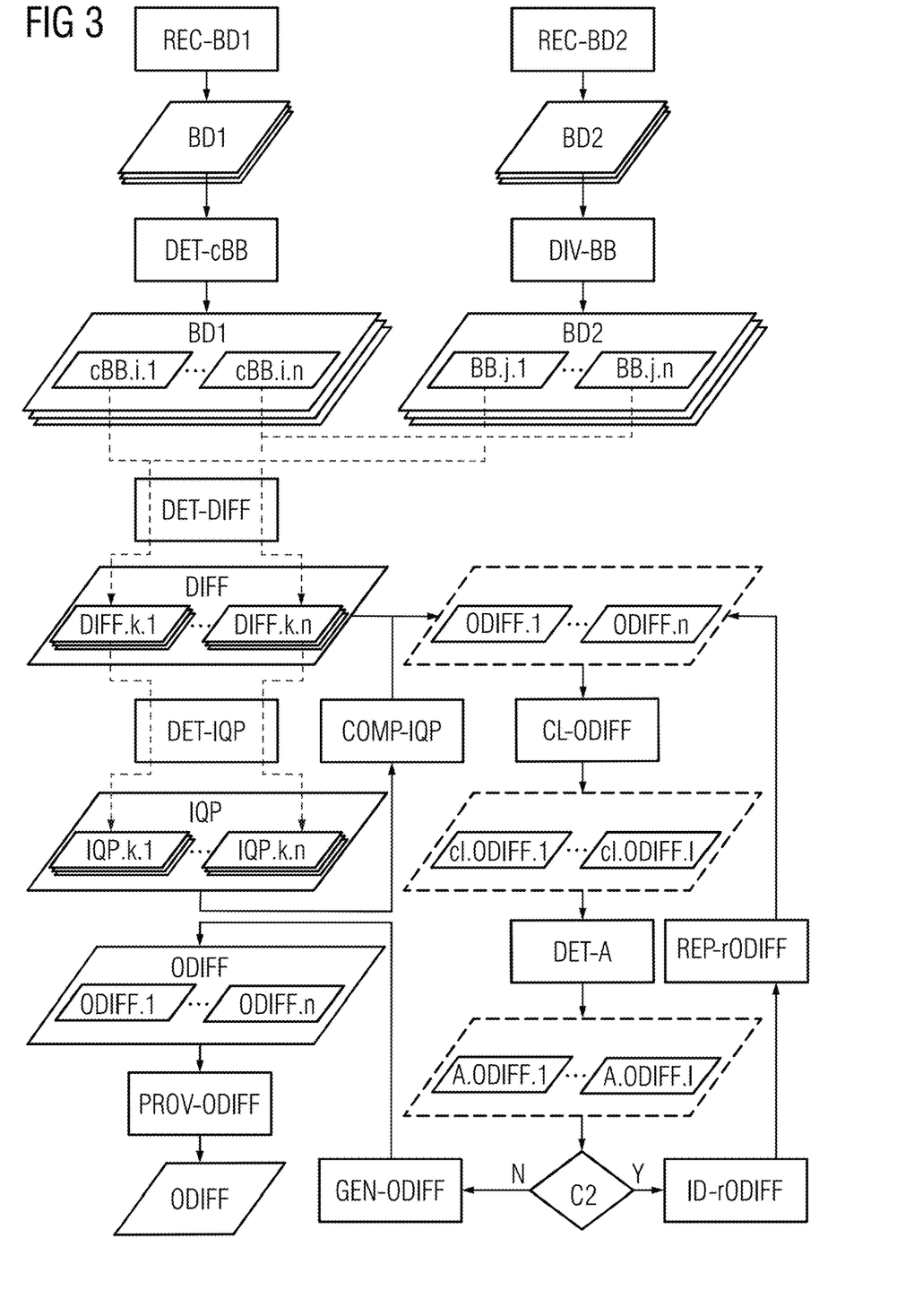

FIG. 3 schematically illustrates another advantageous embodiment of a proposed method for the provision PROV-ODIFF of an optimum subtraction data set ODIFF. Here, the proposed method may include act f.3), wherein the optimum subtraction image regions ODIFF.1 to ODIFF.n may be classified CL-ODIFF into spatially coherent and spatially isolated optimum subtraction image regions cl.ODIFF.1 to cl.ODIFF.1. For example, the optimum subtraction image regions ODIFF.1 to ODIFF.n may be classified into a number 1 of spatially classified optimum subtraction image regions cl.ODIFF.1 to cl.ODIFF.1. Spatially adjacent optimum subtraction image regions ODIFF.1 to ODIFF.n which were generated by the same first image data set BD1 may be classified CL-ODIFF as spatially coherent. In addition, optimum subtraction image regions ODIFF.1 to ODIFF.n without a spatially adjacent optimum subtraction image region ODIFF.1 to ODIFF.n generated by the same first image data set BD1 may be classified CL-ODIFF as spatially isolated. In act f.4), a respective spatial component A.ODIFF.1 to A.ODIFF.1 of the classified optimum subtraction image regions CL.ODIFF.1 to CL.ODIFF.1 may be determined DET-A. In addition, the respective spatial component A.ODIFF.1 to A.ODIFF.1 of the classified optimum subtraction image regions CL.ODIFF.1 to CL.ODIFF.1 may be compared C2 with a comparison component. If the comparison component is undershot Y, the respective at least one optimum subtraction image region ODIFF.1 to ODIFF.n may be replaced REP-rODIFF by the subtraction image region DIFF.k.1 to DIFF.k.n which has a next best image quality parameter IQP.1 to IQP.n. Acts f.3) and f.4) may then be repeated until the spatial components A.ODIFF.1 to A.ODIFF.1 of the classified optimum subtraction image regions CL.ODIFF.1 to CL.ODIFF.1 equal or exceed N the comparison component.

Figure 4:
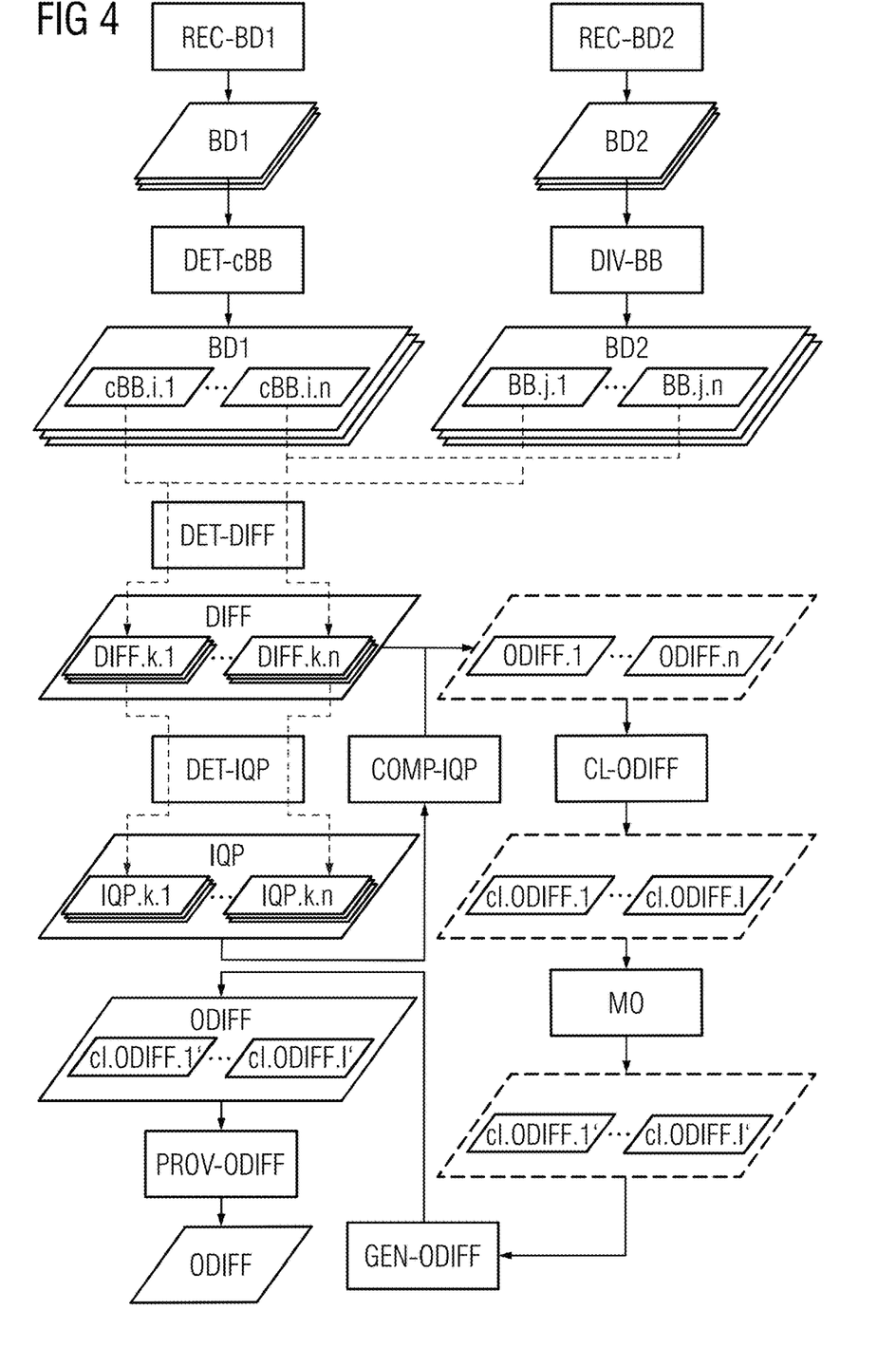

FIG. 4 schematically illustrates another advantageous embodiment of the proposed method for the provision PROV-ODIFF of an optimum subtraction data set ODIFF. Here, in act f), the optimum subtraction image regions ODIFF.1 to ODIFF.n may also be classified CL-ODIFF into spatially coherent and spatially isolated optimum subtraction image regions cl.ODIFF.1 to cl.ODIFF.1. In addition, optimum subtraction image regions classified as spatially isolated may be integrated into an optimum subtraction image region classified as spatially coherent by applying a morphological operation MO. Here, the optimum subtraction image regions cl.ODIFF.1' to cl.ODIFF.1' generated by applying the morphological operation MO may be provided for the generation GEN-ODIFF of the optimum subtraction data set ODIFF in act g).

Figure 5:
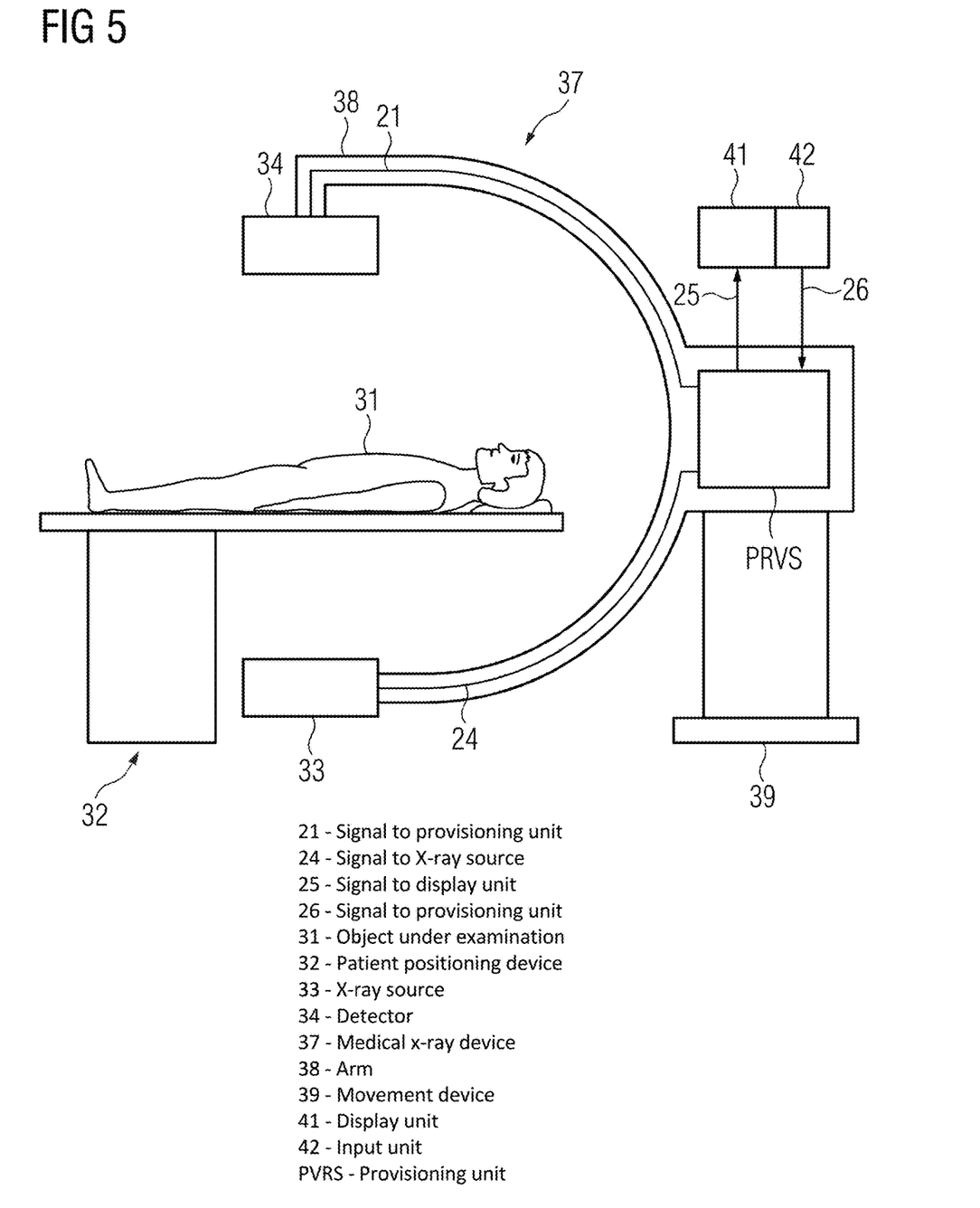
FIG. 5 schematically illustrates a medical C-arm X-ray device as an example of a proposed medical imaging device.

In FIG. 5, a medical C-arm X-ray device 37 is schematically illustrated as an example of a proposed medical imaging device. The medical C-arm X-ray device 37 may advantageously include a provisioning unit PRVS. In addition, the C-arm medical X-ray device 37, in particular the provisioning unit PRVS, may be configured to perform a proposed method for providing PROV-ODIFF an optimum subtraction data set ODIFF.

Here, the medical C-arm X-ray device 37 advantageously includes a detector 34, in particular an X-ray detector, and an X-ray source 33. To acquire the first image data sets BD1 and/or the at least one second image data set BD2, an arm 38 of the C-arm X-ray device 37 may be movably mounted about one or more axes. The medical C-arm X-ray device 37 may also include a movement device 39 that allows the C-arm X-ray device 37 to be moved in the room.

In order to acquire the first image data sets BD1 and/or the at least one second image data set BD2 from an object under examination 31 disposed on a patient positioning device 32, the provisioning unit PRVS may send a signal 24 to the X-ray source 33. In response, the X-ray source 33 may emit an X-ray beam. When, after interacting with the object under examination, the X-ray beam is incident on a surface of the detector 34, the detector 34 may send a signal 21 to the provisioning unit PRVS. On the basis of the signal 21, the provisioning unit PRVS may receive REC-BD1, REC-BD2 the first image data set BD1 and/or the at least one second image data set BD2.

In addition, the medical C-arm X-ray device 37 may include an input unit 42, for example a keyboard, and/or a display unit 41, (e.g., a monitor and/or display). The input unit 42 may be incorporated in the display unit 41, (e.g., in the case of a capacitive and/or resistive input display). A user input to the input unit 42 may be used to control the medical C-arm X-ray device 37, in particular to control the proposed method for the provision PROV-ODIFF of an optimum subtraction data set ODIFF. For this purpose, the input unit 42 may send a signal 26 to the provisioning unit PRVS.

In addition, the display unit 41 may be configured to display information and/or graphical representations of information from the medical C-arm X-ray unit 37 and/or the provisioning unit PRVS and/or other components. For this purpose, the provisioning unit PRVS may send a signal 25 to the display unit 41. In particular, the display unit 41 may be configured to display a graphical representation of the first image data sets BD1 and/or the at least one second image data set BD2 and/or the optimum subtraction data set ODIFF.

The schematic representations contained in the figures described do not indicate any scale or size relationship.

Finally, the methods described in detail above and the devices illustrated are merely exemplary embodiments which may be modified by persons skilled in the art in a wide variety of ways without departing from the scope of the disclosure. Moreover, the use of the indefinite articles "a" or "an" does not exclude the possibility that the features in question may be present more than once. Likewise, the terms "unit" and "element" do not exclude the possibility that the components in question include a plurality of interacting sub-components which may possibly also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing an optimum subtraction data set, the method comprising:

receiving first image data sets that map an object under examination within a first time phase, wherein the first image data sets are acquired by a medical imaging device;

receiving at least one second image data set that maps the object under examination within a second time phase, wherein the at least one second image data set is acquired by a same medical imaging device or another medical imaging device, and wherein the at least one second image data set maps a change in the object under examination with respect to the first time phase;

dividing the at least one second image data set into a plurality of spatial image regions;

generating subtraction image regions for the plurality of spatial image regions by subtracting corresponding image regions of the first image data sets from each image region of the plurality of spatial image regions of the at least one second image data set;

determining an image quality parameter for each subtraction image region of the subtraction image regions;

determining an optimum subtraction image region for each image region of the plurality of spatial image regions of the at least one second image data set by a comparison of the image quality parameters;

generating the optimum subtraction data set from the optimum subtraction image regions; and providing the optimum subtraction data set.

2. The method of claim 1, wherein the determining of the optimum subtraction image region comprises:
checking whether a number of first image data sets used to generate the optimum subtraction image regions exceeds a predetermined threshold value;
identifying a first image data set of the first image data sets that was used least frequently to generate the optimum subtraction image regions when the number of first image data sets exceeds the predetermined threshold value; and
replacing the optimum subtraction image region generated by the identified first image data set by the subtraction image region having a next best image quality parameter,
wherein the checking is repeated until the predetermined threshold value is reached or undershot.

3. The method of claim 1, wherein the determining of the optimum subtraction image region comprises:
classifying the optimum subtraction image regions into spatially coherent and spatially isolated optimum subtraction image regions, wherein spatially adjacent optimum subtraction image regions generated using a same first image data set are classified as spatially coherent, wherein optimum subtraction image regions without a spatially adjacent optimum subtraction image region generated using the same first image data set are classified as spatially isolated; and
comparing a spatial component of each classified optimum subtraction image region of the classified optimum subtraction image regions with a comparison component,
wherein, when the comparison component is undershot, the respective optimum subtraction image region is replaced by a subtraction image region having a next best image quality parameter, and
wherein the classifying and the comparing are repeated until the spatial components of the classified optimum subtraction image equal or exceed the comparison component.

4. The method of claim 3, wherein optimum subtraction image regions classified as spatially isolated are integrated into an optimum subtraction image region classified as spatially coherent by applying a morphological operation.

5. The method of claim 1, wherein the determining of the optimum subtraction image region comprises:
classifying the optimum subtraction image regions into spatially coherent and spatially isolated optimum subtraction image regions,
wherein spatially adjacent optimum subtraction image regions generated using a same first image data set are classified as spatially coherent,
wherein optimum subtraction image regions without a spatially adjacent optimum subtraction image region generated using the same first image data set are classified as spatially isolated, and
wherein optimum subtraction image regions classified as spatially isolated are integrated into an optimum subtraction image region classified as spatially coherent by applying a morphological operation.

6. The method of claim 1, wherein the generating of the subtraction image regions comprises registering the image regions of the at least one second image data set with the corresponding image regions of the first image data sets.

7. The method of claim 1, wherein the generating of the optimum subtraction data set comprises combining respective spatially adjacent optimum subtraction image regions in at least one common edge region.

8. The method of claim 1, wherein the dividing of the at least one second image data set into the plurality of spatial image regions is carried out based on anatomical features and/or geometrical features which are mapped in the at least one second image data set.

9. The method of claim 1, wherein the at least one second image data set maps a contrast agent disposed in the object under examination in the second time phase as the change.

10. The method of claim 1, wherein the image quality parameters are determined by applying an image quality metric to each of the subtraction image regions, and
wherein the image quality metric evaluates an artifact level and/or signal-to-noise ratio in the respective subtraction image region.

11. The method of claim 10, wherein the image quality metric is based on artificial intelligence.

12. The method of claim 1, wherein the medical imaging device and/or the other medical imaging device is a medical X-ray device, a computed tomography device, a magnetic resonance device, a positron emission tomography device, an ultrasound device, or a combination thereof.

13. A medical imaging device comprising:
a processor configured to:
receive first image data sets that map an object under examination within a first time phase, wherein the first image data sets are acquired by the medical imaging device;
receive at least one second image data set that maps the object under examination within a second time phase, wherein the at least one second image data set is acquired by the medical imaging device or another medical imaging device, and wherein the at least one second image data set maps a change in the object under examination with respect to the first time phase;
divide the at least one second image data set into a plurality of spatial image regions;
generate subtraction image regions for the plurality of spatial image regions by subtracting corresponding image regions of the first image data sets from each image region of the plurality of spatial image regions of the at least one second image data set;

determine an image quality parameter for each subtraction image region of the subtraction image regions;

determine an optimum subtraction image region for each image region of the plurality of spatial image regions of the at least one second image data set by a comparison of the image quality parameters;

generate an optimum subtraction data set from the optimum subtraction image regions; and provide the optimum subtraction data set.

14. A non-transitory computer program product comprising a program configured to be directly loaded into a memory of a programmable processor of a medical imaging device, wherein the program, when executed in the processor, is configured to cause the medical imaging device to:

receive first image data sets that map an object under examination within a first time phase, wherein the first image data sets are acquired by the medical imaging device;

receive at least one second image data set that maps the object under examination within a second time phase, wherein the at least one second image data set is acquired by a same or another medical imaging device, and wherein the at least one second image data set maps a change in the object under examination with respect to the first time phase;

divide the at least one second image data set into a plurality of spatial image regions;

generate subtraction image regions for the plurality of spatial image regions by subtracting corresponding image regions of the first image data sets from each image region of the plurality of spatial image regions of the at least one second image data set;

determine an image quality parameter for each subtraction image region of the subtraction image regions;

determine an optimum subtraction image region for each image region of the plurality of spatial image regions of the at least one second image data set by a comparison of the image quality parameters;

generate an optimum subtraction data set from the optimum subtraction image regions; and provide the optimum subtraction data set.

15. The method of claim 2, wherein the determining of the optimum subtraction image region further comprises:

classifying the optimum subtraction image regions into spatially coherent and spatially isolated optimum subtraction image regions, wherein spatially adjacent optimum subtraction image regions generated using a same first image data set are classified as spatially coherent, wherein optimum subtraction image regions without a spatially adjacent optimum subtraction image region generated using the same first image data set are classified as spatially isolated; and comparing a spatial component of each classified optimum subtraction image region of the classified optimum subtraction image regions with a comparison component, wherein, when the comparison component is undershot, the respective optimum subtraction image region is replaced by a subtraction image region having a next best image quality parameter, and wherein the classifying and the comparing are repeated until the spatial components of the classified optimum subtraction image equal or exceed the comparison component.

16. The method of claim 15, wherein optimum subtraction image regions classified as spatially isolated are integrated into an optimum subtraction image region classified as spatially coherent by applying a morphological operation.

17. The method of claim 2, wherein the determining of the optimum subtraction image region further comprises:

classifying the optimum subtraction image regions into spatially coherent and spatially isolated optimum subtraction image regions, wherein spatially adjacent optimum subtraction image regions generated using a same first image data set are classified as spatially coherent, wherein optimum subtraction image regions without a spatially adjacent optimum subtraction image region generated using the same first image data set are classified as spatially isolated, and wherein optimum subtraction image regions classified as spatially isolated are integrated into an optimum subtraction image region classified as spatially coherent by applying a morphological operation.

18. The method of claim 2, wherein the generating of the subtraction image regions comprises registering the image regions of the at least one second image data set with the corresponding image regions of the first image data sets.

19. The method of claim 2, wherein the generating of the optimum subtraction data set comprises combining respective spatially adjacent optimum subtraction image regions in at least one common edge region.

20. The method of claim 2, wherein the dividing of the at least one second image data set into the plurality of spatial image regions is carried out based on anatomical features and/or geometrical features which are mapped in the at least one second image data set.

* * * * *

UNITED STATES PATENT AND TRADEMARK OFFICE
CERTIFICATE OF CORRECTION

| | |
|---|---|
| PATENT NO. | : 11,455,711 B2 |
| APPLICATION NO. | : 17/510935 |
| DATED | : September 27, 2022 |
| INVENTOR(S) | : Michael Manhart |

It is certified that error appears in the above-identified patent and that said Letters Patent is hereby corrected as shown below:

On the Title Page

Item (30) Foreign Application Priority Data:
"(DE) ..................... 10 2020 214 319.8"
Should be replaced with:
"(DE) ..................... 10 2020 214 319.6"

Signed and Sealed this
Fifteenth Day of November, 2022

Katherine Kelly Vidal
*Director of the United States Patent and Trademark Office*